US009393050B2

(12) United States Patent
Karas et al.

(10) Patent No.: US 9,393,050 B2
(45) Date of Patent: Jul. 19, 2016

(54) SYSTEMS, METHODS, AND APPARATUSES FOR SPINAL FIXATION

(75) Inventors: Chris Karas, Columbus, OH (US); Ryan Leard, Oakland, CA (US); Sebastian Lodahl, Oakland, CA (US)

(73) Assignee: Awesome Dudes Making Tools, LLC, Columbus, OH (US)

( * ) Notice: Subject to any disclaimer, the term of this patent is extended or adjusted under 35 U.S.C. 154(b) by 0 days.

(21) Appl. No.: 13/561,006

(22) Filed: Jul. 28, 2012

(65) Prior Publication Data

US 2013/0030469 A1 Jan. 31, 2013

Related U.S. Application Data

(60) Provisional application No. 61/574,070, filed on Jul. 28, 2011, provisional application No. 61/676,129, filed on Jul. 26, 2012.

(51) Int. Cl.
*A61B 17/88* (2006.01)
*A61B 17/70* (2006.01)
*A61B 17/17* (2006.01)
(Continued)

(52) U.S. Cl.
CPC ......... *A61B 17/7049* (2013.01); *A61B 17/1757* (2013.01); *A61B 17/707* (2013.01); *A61B 17/7035* (2013.01); *A61B 17/844* (2013.01); *A61B 17/864* (2013.01)

(58) Field of Classification Search
CPC ........... A61B 17/7041; A61B 17/7008; A61B 17/7082; A61B 17/7083; A61B 2017/681; A61B 17/7067; A61B 17/7068; A61B 17/7076; A61B 17/809; A61B 17/86; A61B 17/8897; A61B 17/7062; A61B 17/846; A61B 17/7049; A61B 17/1757; A61B 17/7035; A61B 17/707; A61B 17/844; A61B 17/864
USPC ................ 606/86 R, 86 A, 99, 250, 264, 279
See application file for complete search history.

(56) References Cited

U.S. PATENT DOCUMENTS 5,171,279 A 12/1992 Mathews
5,330,473 A 7/1994 Howland
(Continued)

FOREIGN PATENT DOCUMENTS

BR PI0904658-5 A2 11/2010

OTHER PUBLICATIONS

Dynesys® Dynamic Syabilization Product Family. Product Overview [online]. Zimmer, Inc., Zimmer Spine, unknown date [retrieved on Mar. 2, 2014]. Retrieved from the Internet: <URL: http://www.zimmer.com/en-US/hcp/spine/product/dynesys-dynamic-stabilization-system.jspx>.

(Continued)

*Primary Examiner* — Mary Hoffman
*Assistant Examiner* — Tara R Carter
(74) *Attorney, Agent, or Firm* — Benesch Friedlander Coplan & Aronoff, LLP; Benjamen E. Kern; Thomas Y. Kendrick

(57) ABSTRACT

Methods, systems, and apparatuses are disclosed for spinal fixation. In one example embodiment, a minimally invasive crosslink apparatus with an elongated shaft portion, a self-drilling tip portion, and a posterolateral delivery device is provided. In this example embodiment, the elongated shaft portion is configured to connect to at least one of a vertical fixation rod and a pedicle screw head.

18 Claims, 6 Drawing Sheets

(51) Int. Cl.
*A61B 17/84* (2006.01)
*A61B 17/86* (2006.01)

(56) References Cited

U.S. PATENT DOCUMENTS

| | | | |
|---|---|---|---|
| 5,380,325 | A | 1/1995 | Lahille et al. |
| 5,470,333 | A * | 11/1995 | Ray .................... A61B 17/7055 606/261 |
| 5,928,236 | A | 7/1999 | Augagneur et al. |
| 6,068,630 | A | 5/2000 | Zucherman et al. |
| 6,139,548 | A | 10/2000 | Errico |
| 7,247,171 | B2 | 7/2007 | Sotereanos |
| 7,763,051 | B2 | 7/2010 | Labrom et al. |
| 7,766,920 | B2 * | 8/2010 | Ciccone et al. ............... 606/104 |
| 7,951,198 | B2 | 5/2011 | Sucec et al. |
| 7,955,388 | B2 | 6/2011 | Jensen et al. |
| 8,123,785 | B2 | 2/2012 | Weaver et al. |
| 8,303,629 | B1 | 11/2012 | Abdou |
| 8,460,301 | B2 * | 6/2013 | Fiorella ........................ 606/86 A |
| 2005/0267473 | A1 | 12/2005 | Vaughan |
| 2006/0058790 | A1 * | 3/2006 | Carl et al. ........................ 606/61 |
| 2006/0241621 | A1 | 10/2006 | Moskowitz et al. |
| 2007/0118120 | A1 * | 5/2007 | Stevenson et al. ............... 606/61 |
| 2007/0213714 | A1 * | 9/2007 | Justis ............................... 606/61 |
| 2008/0091205 | A1 | 4/2008 | Kuiper et al. |
| 2008/0269805 | A1 * | 10/2008 | Dekutoski et al. ............ 606/279 |
| 2008/0281359 | A1 | 11/2008 | Abdou |
| 2009/0234390 | A1 | 9/2009 | Poirier et al. |
| 2010/0069965 | A1 | 3/2010 | Abdou |
| 2011/0106161 | A1 | 5/2011 | Wilcox et al. |
| 2011/0125265 | A1 | 5/2011 | Bagga et al. |
| 2012/0010668 | A1 | 1/2012 | Shimko |
| 2012/0071985 | A1 | 3/2012 | Hodorek et al. |

OTHER PUBLICATIONS

LimiFlex® Spinal Stabilization System. Product Overview [online]. Simpirica Spine, Inc., unknown date [retrieved on Mar. 2, 2014]. Retrieved from the Internet: <URL: http://www.simpirica.com/us-en/patients/limiflex-spinal-stabilization-system.php>.

OsseoScrew™ Spinal Fixation System. Product Overview [online]. Alphatec Spince Inc., unknown date [retrieved on Mar. 2, 2014]. Retrieved from the Internet: <URL: http://www.alphatecspine.com/products/osseoscrew.asp>.

International Search Report and Written Opinion for PCT/US2013/052271. Nov. 8, 2013.

* cited by examiner

SYSTEMS, METHODS, AND APPARATUSES FOR SPINAL FIXATION

CROSS-REFERENCE TO RELATED APPLICATIONS

This application claims priority from U.S. Provisional Patent Application No. 61/574,070, filed on Jul. 28, 2011, and U.S. Provisional Patent Application No. 61/676,129, filed on Jul. 26, 2012, each of which is incorporated by reference herein in its entirety.

BACKGROUND

The purpose of spinal fixation is to strengthen and stabilize the spine to alleviate severe and chronic back pain. Spinal fixation is generally the anchoring of two or more vertebrae to each other employing instrumentation. This procedure may be performed open or employing a minimally invasive technique. Fixation is usually performed at a single vertebral level, although fusion at two levels may be performed. Fixation also often involves the use of supplemental hardware such as plates, screws, and cages.

Approximately 453,300 spinal fixation procedures are performed annually in the US. Currently, an increasing number of spinal surgical procedures are performed each year, especially lumbar spinal fusions. In particular, the growth in the number of lumbar spinal fusions in the population over age 60 is noted as "remarkable," growing from 42/100,000 in 1993 to 108/100,000 in 2003.

One estimate posits that approximately 5 million adults in the United States are currently disabled to some degree from spine-related disorders, indicating a large potential group requiring interventions.

Minimally Invasive Crosslink Apparatus

The use of crosslink members between vertical fixation rods increases the stability of spinal fixation constructs in the cervical, thoracic, and lumbar spine. However, implantation of such crosslinks traditionally requires removal of potentially healthy tissue between pedicle screws and/or vertical fixation rods. What is needed is a minimally invasive crosslink member and a method of installing the same that does not require the removal of intervening healthy tissue from the surgical site.

Multi-Level Spinous Process Fixation System

Spinous process fixation is a desirable technique for spinal fusion in a number of instances, including those where a pedicle does not exist to accept a pedicle screw, those where operative time and radiation exposure need to be minimized, and those where fixation needs to be achieved adjacent to a previous pedicle screw and rod construct. However, adjacent level fixation has previously required removal of preexisting pedicle constructs in order to install new pedicle screws and rods, resulting in unnecessarily complex surgeries and additional tissue trauma. Furthermore, previous spinous process fixation was not capable of tying into preexisting pedicle constructs. What is needed is an apparatus configured to work with preexisting pedicle constructs and tie spinous process constructs thereto and to each other.

Pedicle Replacement System

The pedicle portion of a vertebra is commonly used as an anchor point for pedicle screws when utilizing pedicle constructs for spinal fixation. However, for a number of reasons a pedicle may not be capable of acting as an anchor point, which previously required more complicated fixation constructs. For example, a pedicle that has previously been weakened by a pedicle screw may not have the strength to act as an anchor during installation of a later construct. Additionally, various diseases such as tumors or osteoporosis may causes weakening or deterioration of the pedicle. What is needed is a prosthetic pedicle capable of installation in the place of a previously-existing pedicle and having the requisite strength to act as an anchor point in a pedicle construct.

SUMMARY

In one embodiment, a minimally invasive crosslink apparatus is provided, the apparatus comprising: an elongated shaft portion; a self-drilling tip portion; and a posterolateral delivery device; wherein the elongated shaft portion is configured to connect to at least one of a vertical fixation rod and a pedicle screw head.

In another embodiment, a system for spinal fusion is provided, the system comprising: a minimally invasive crosslink apparatus comprising an elongated shaft portion and a self-drilling tip portion; at least one of a vertical fixation rod and a pedicle screw set screw; and wherein the elongated shaft portion is connected to at least one of the vertical fixation rod and the pedicle screw set screw.

In another embodiment, a method for installing a minimally invasive crosslink apparatus for spinal fusion is provided, the method comprising: providing a pedicle screw construct comprising at least one pedicle screw set screw and at least one vertical fixation rod; providing a minimally invasive crosslink apparatus comprising an elongated shaft portion and a self-drilling tip portion; connecting at least one acceptor component to one or more of the at least one pedicle screw set screw and the at least one vertical fixation rod; connecting the minimally invasive crosslink apparatus to a driver device; activating the driver device to cause at least one of a torque and a lateral force upon the self-drilling tip portion; advancing the minimally invasive crosslink apparatus along its longitudinal axis: (1) medially from a first side of the spinal column in plane substantially parallel to a frontal plane, (2) across the midsagittal plane, and (3) laterally to a second side of the spinal column in a plane substantially parallel to the frontal plane; and connecting the elongated shaft portion to the at least one acceptor component.

In one embodiment, a spinous process clamp apparatus is provided, the apparatus comprising: a pair of plates, wherein a medial surface of each plate of the pair of plates is configured to contact at least one spinous process; a plate locking mechanism configured to apply a compressive force upon each of the pair of plates; and a rod acceptor.

In another embodiment, a system for stabilization of a spinous process is provided, the system comprising: a spinous process clamp apparatus comprising: a pair of plates, a plate locking mechanism configured to apply a compressive force upon each of the pair of plates, and a rod acceptor; and at least one of a vertical rod, a horizontal rod, and a multiaxial rod; wherein the rod acceptor is connected to at least one of the vertical rod, the horizontal rod, and the multiaxial rod.

In another embodiment, a system for stabilization of a spinous process is provided, the system comprising: a spinous process clamp apparatus comprising: a pair of plates configured to contact at least one spinous process, a plate locking mechanism configured to apply a compressive force upon each of the pair of plates, and a rod acceptor; and a pedicle screw construct comprising at least one of a vertical fixation rod, a horizontal fixation rod, and a pedicle screw; wherein the rod acceptor is selectively connected to at least one of the vertical fixation rod, the horizontal fixation rod, and the pedicle screw.

In one embodiment, a pedicle prosthesis apparatus is provided, the apparatus comprising: a pedicle portion configured to extend from a vertebral body; a shaft portion configured to extend into the vertebral body; and wherein the pedicle portion is substantially smooth about its exterior.

In another embodiment, a system for replacement of a pedicle of a vertebral body is provided, the system comprising: a pedicle prosthesis apparatus comprising a pedicle portion, a shaft portion, and a substantially smooth exterior; and at least one pedicle screw.

BRIEF DESCRIPTION OF THE DRAWINGS

The accompanying figures, which are incorporated in and constitute a part of the specification, illustrate various example apparatuses, systems, and methods, and are used merely to illustrate various example embodiments.

DETAILED DESCRIPTION

Minimally Invasive Crosslink Apparatus

Figure 1:
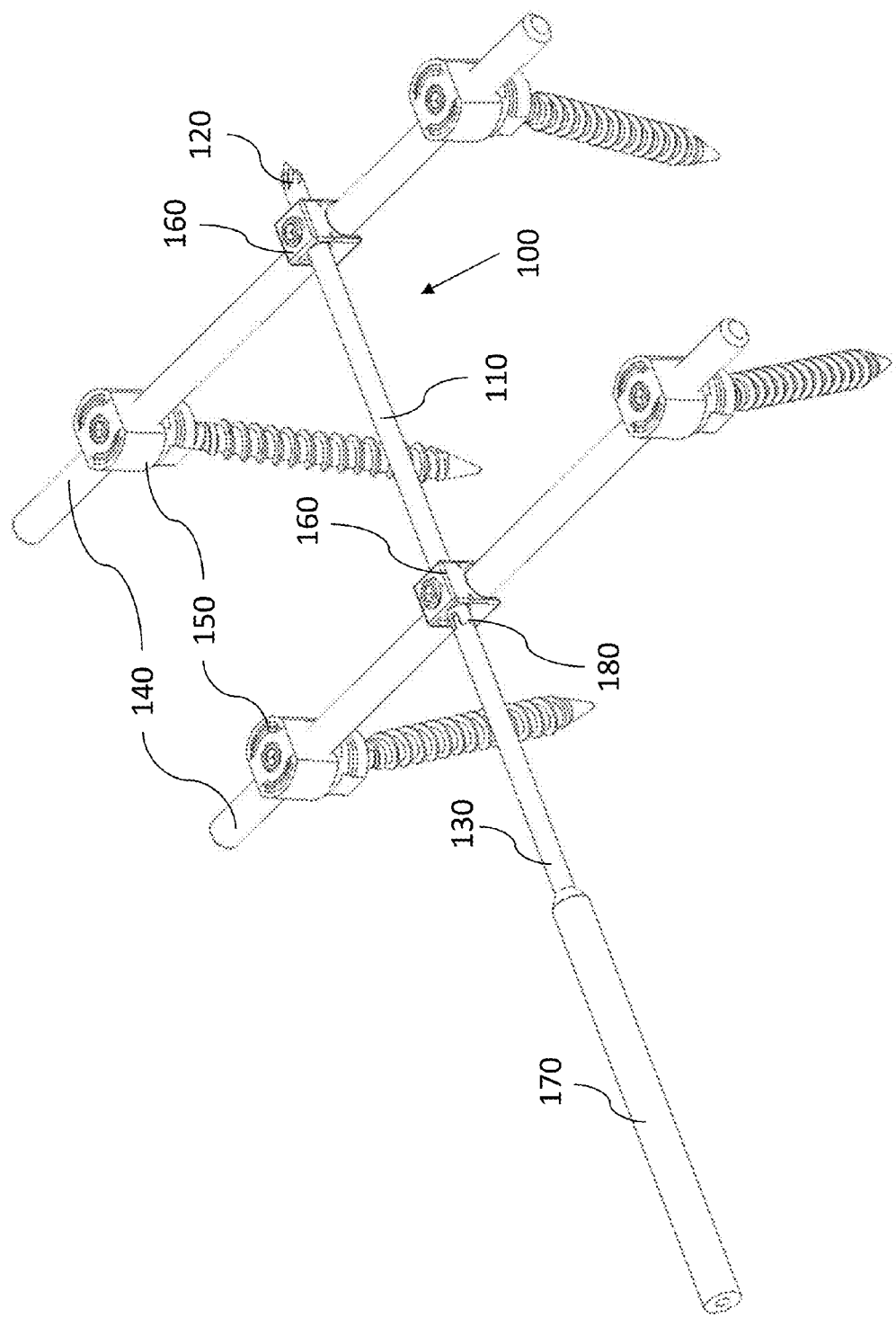
FIG. 1 illustrates an example arrangement of a minimally invasive crosslink apparatus.

FIG. 1 illustrates an example arrangement of a minimally invasive crosslink apparatus 100. Apparatus 100 may include an elongated shaft portion 110, a self-drilling tip portion 120, and a posterolateral delivery device 130. Elongated shaft portion 110 may be configured to connect to at least one of a vertical fixation rod 140 and a spinal fixative device 150.

Apparatus 100 may comprise a horizontal crosslink apparatus. Such horizontal crosslink apparatus may be configured to connect at least two vertical fixation rods 140 to one another to improve the stability and/or torsional rigidity of a spinal fixation construct. In one embodiment, elongated shaft portion 110 connects to vertical fixation rod 140 via at least one acceptor component 160. In another embodiment, apparatus 100 extends between and connects to two vertical fixation rods 140 via acceptor components 160.

In one embodiment, elongated shaft portion 110 is configured to extend from a first acceptor component 160 attached to a first vertical fixation rod 140, through an anatomic structure, and to a second acceptor component 160 attached to a second vertical fixation rod 140. In another embodiment, elongated shaft portion 110 is configured to extend from a first spinal fixative device 150, through an anatomic structure, and to a second spinal fixative device 150. In another embodiment, elongated shaft portion 110 is configured to connect to any combination of at least one of a vertical fixation rod 140, acceptor components 160, pedicle screws, pedicle screw heads, or other fixation devices. In one embodiment, elongated shaft portion 110 is secured to any of the acceptor component 160, vertical fixation rod 140 and spinal fixative device 150 by a fastener, for example, a screw or a nut. In another embodiment, elongated shaft portion 110 is secured by any of a series of fasteners or attachment mechanisms, including for example, a clamp, a cable, a strap, a barbed connector, or an adhesive. Elongated shaft 110 may comprise any material, including a metal, a polymer, or a composite.

Spinal fixative device 150 may include a pedicle screw and/or pedicle screw head. In one embodiment, the pedicle screw head comprises at least one pedicle screw set screw configured to engage at least one of vertical fixation rod 140 and elongated shaft portion 110. In one embodiment, at least one acceptor component 160 comprises a fastener configured to attach elongated shaft portion 110, directly or operatively, to at least one of vertical fixation rod 140 and pedicle screw head.

In one embodiment, self-drilling tip portion 120 comprises a fluted end. In another embodiment, self-drilling tip portion 120 comprises a cutting end, such that rotation of self-drilling tip portion 120 causes self-drilling tip portion 120 to bore a hole in a material. In one embodiment, self-drilling tip portion 120 is configured to create a passage for elongated shaft portion 110 through at least one of a hard tissue and a soft tissue. In another embodiment, self-drilling tip portion 120 is configured to create a passage for elongated shaft portion 110 through at least one of bone, muscle, fascia, and fat. Self-drilling tip portion 120 may be capable of selectively drilling a passage either partially though a material or entirely through a material. In one embodiment, self-drilling tip portion 120 may comprise a sharpened and/or pointed end configured to be driven or pressed through a material substantially without rotational force and utilizing a substantially lateral force.

In one embodiment, posterolateral delivery device 130 comprises a driver engagement portion 170 configured to connect posterolateral delivery device 130 to a driver device (not shown). Driver engagement portion 170 may comprise for example a screw head or a bolt head upon which a driver device may be engaged. In one embodiment, the driver device is configured to cause a torque upon self-drilling tip portion 120 about a longitudinal axis of elongated shaft portion 120. In another embodiment, the driver device is configured to cause a lateral force upon self-drilling tip portion 120 along a longitudinal axis of elongated shaft portion 120. The torque and/or lateral force applied upon self-drilling tip portion 120 may cause self-drilling tip portion 120 to create a passage for elongated shaft portion 110 through at least one of a hard tissue or a soft tissue, including for example bone, muscle, fascia, and fat.

In one embodiment, posterolateral delivery device 130 is selectively removable from elongated shaft portion 110. In another embodiment, posterolateral delivery device 130 may be separated from elongated shaft portion 110 at posterolateral delivery device connection joint 180. Joint 180 may include for example a threaded joint, a scored joint configured to break under a stress, or a point at which posterolateral delivery device 130 may be cut and removed from elongated shaft portion 110. In another embodiment, joint 180 includes a male and female portion. In another embodiment, joint 180 includes a clamp configured to join posterolateral delivery device 130 to elongated shaft portion 110. In another embodiment, posterolateral delivery device 130 may be configured to selectively reattach to elongated shaft portion 110.

Figure 2:
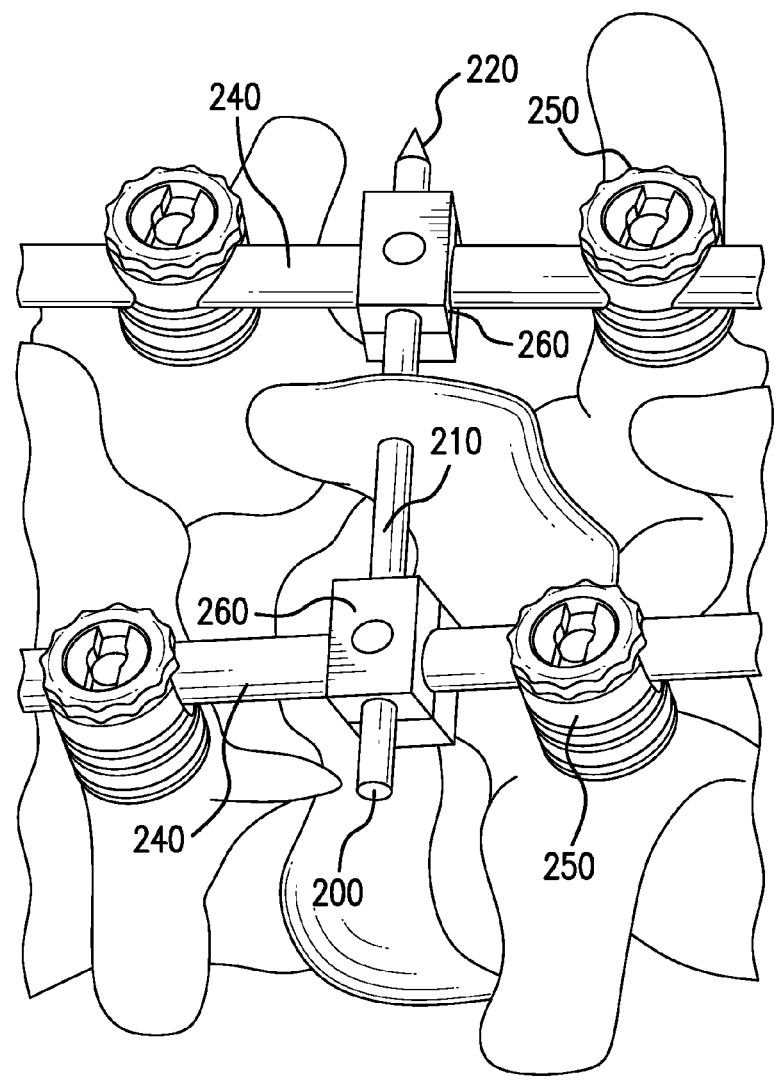
FIG. 2 illustrates an example arrangement of a system for spinal fusion.

FIG. 2 illustrates an example arrangement of a system for spinal fusion. The system includes a minimally invasive crosslink apparatus 200 having an elongated shaft portion 210 and a self-drilling tip portion 220. The system may include a vertical fixation rod 240. The system may also include a pedicle screw set screw 250. Elongated shaft portion 210 may be connected to at least one of vertical fixation rod 240 and pedicle screw set screw 250. The system may also include at least one acceptor component 260.

Minimally invasive crosslink apparatus 100 and 200 may be a horizontal crosslink configured to increase the stability of constructs in the cervical, thoracic, and lumbar spine. Prior systems required a non-minimally invasive implantation of a crosslink, requiring removal of hard and soft tissue situated between a set of pedicle screw heads or vertical fixation rods within a pedicle screw construct. Removal of this tissue was necessary to gain access to the construct for installation of the crosslink. After this tissue was removed, a crosslink could be installed from the posterior or anterior side of the spine.

However, minimally invasive systems have been developed to allow for minimally invasive placement of thoracic and lumbar pedicle screw and rod constructs. In the installation of such minimally invasive systems, the tissue situated between a set of pedicle screw heads or vertical fixation rods is not removed, as the minimally invasive approach seeks to cause the least amount of disturbance possible to healthy tissues. In using such a system, a crosslink cannot be installed from the posterior or anterior side of the spine.

Accordingly, minimally invasive crosslink apparatus 100 and 200 may be installed medially from a side of the spinal column and substantially parallel to its frontal plane, across the midsagittal plane, and laterally to an opposite side of the spinal column. In installing the minimally invasive crosslink apparatus 100 and 200 in such a manner, the potentially healthy tissue situated between a set of pedicle screw heads or vertical fixation rods need not be removed.

In one embodiment, method for installing minimally invasive crosslink apparatus 200 for spinal fusion is provided, the method comprising: providing a pedicle screw construct comprising at least one pedicle screw set screw 250 and at least one vertical fixation rod 240. The method additionally includes providing minimally invasive crosslink apparatus 200 comprising elongated shaft portion 210 and self-drilling tip portion 220. The method further comprises connecting at least one acceptor component 260 to one or more of at least one pedicle screw set screw 250 and at least one vertical fixation rod 240. The method additionally includes connecting minimally invasive crosslink apparatus 200 to a driver device (not shown) and activating the driver device to cause a torque upon self-drilling tip portion 220. The method also comprises advancing minimally invasive crosslink apparatus 200 along its longitudinal axis: (1) medially from a first side of the spinal column in plane substantially parallel to a frontal plane, (2) across the midsagittal plane, and (3) laterally to a second side of the spinal column in a plane substantially parallel to the frontal plane. Finally, the method may include connecting elongated shaft portion 210 to at least one acceptor component 260.

The method may additionally include a posterolateral delivery device (not shown) connected to minimally invasive crosslink apparatus 200 and connected to the driver device. In one embodiment, the method also includes removing the posterolateral delivery device from minimally invasive crosslink apparatus 200 following the advancing of minimally invasive crosslink apparatus 200 along its longitudinal axis. In another embodiment, the advancing minimally invasive crosslink apparatus 200 along its longitudinal axis further comprises causing self-drilling tip portion 220 to create a passage for elongated shaft portion 210 through at least one of a hard tissue and a soft tissue. In another embodiment, the advancing minimally invasive crosslink apparatus 500 along its longitudinal axis further comprises causing self-drilling tip portion 220 to pass through at least one acceptor component 260. In one embodiment, self-drilling tip portion 220 includes a sharpened and/or pointed tip and the activating the driver device is configured to cause a lateral force upon self-drilling tip portion 220, instead of or in addition to causing a torque upon self-drilling tip portion 220.

Figure 3:
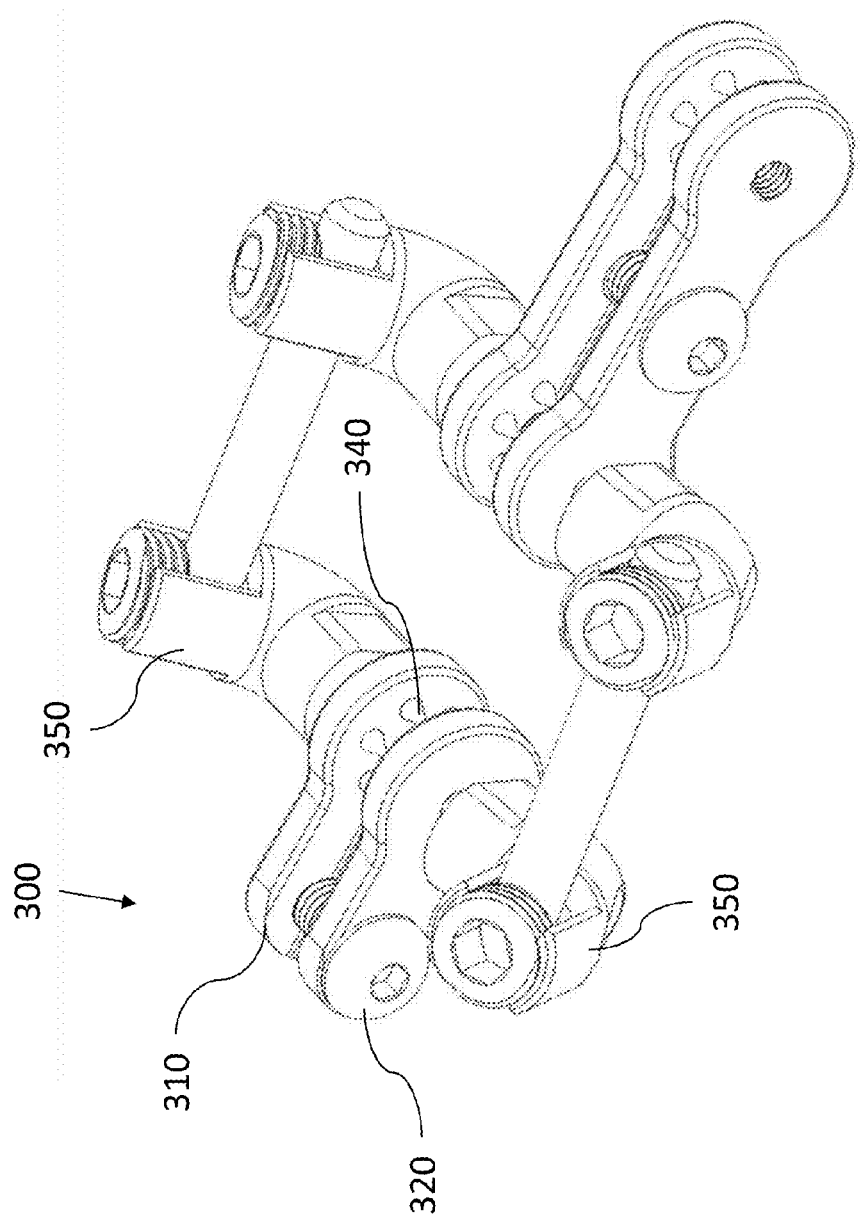
FIG. 3 illustrates an example arrangement of a spinous process clamp apparatus.

FIG. 3 illustrates an example arrangement of a spinous process clamp apparatus 300. Apparatus 300 comprises a pair of plates 310, wherein the medial surface of each plate is configured to contact at least one spinous process. Apparatus 300 may additionally comprise a plate locking mechanism 320 configured to apply compressive force upon each of the pair of plates 310. At least one of pair of plates 310 may comprise bone spikes 340. Apparatus 300 may additionally comprise a rod acceptor 350.

Plates 310 may be of any size or configuration to allow a connection to at least one spinous process (not shown). For example, plates 310 may comprise a dog bone shape having larger terminal ends with a narrower central portion. In one embodiment, plates 310 comprise a single spinous process clamp, having only a single end portion configured for attachment to a construct. In another embodiment, plates 310 comprise a dual spinous process clamp, having two end portions configured for attachment to a construct. In one embodiment, at least one of plates 310 comprises a medial surface comprising bone spikes 340. Plates 310 may comprise any of a variety of materials, including for example a metal, a polymer, or a composite.

In one embodiment, plate locking mechanism 320 comprises a selectively engageable locking mechanism. In another embodiment, plate locking mechanism 320 comprises a barbed mechanism that can be inserted through an aperture in the pair of plates 310 wherein the barbs engage the pair of plates 310 and apply compressive forces upon each of pair of plates 310. In one embodiment, plate locking mechanism 320 comprises any fastener device capable of applying a compressive force upon each of pair of plates 310, including a screw, a nut, a cable, a strap, a clamp, a barbed connector, and an adhesive.

In one embodiment, apparatus 300 comprises rod acceptor 350, wherein rod acceptor 350 is configured to attach to at least one of a vertical rod, a horizontal rod, and a multiaxial rod. In one embodiment, the horizontal rod is a horizontal crosslink. In another embodiment, rod acceptor 350 is configured to operatively connect to at least one of a pedicle screw, a pedicle screw set screw, and a spinal fixative device. Rod acceptor 350 may additionally comprise at least one rod acceptor locking screw configured to engage at least one of a vertical rod, a horizontal rod, and a multiaxial rod and at least substantially prevent relative movement between rod acceptor 350 and the vertical rod, horizontal rod, and/or multiaxial rod. A multiaxial rod comprises any rod that is not substantially vertical or substantially horizontal In one embodiment, rod acceptor 350 is a vertical rod acceptor configured to connect plates 310 to at least one vertical fixation rod. In another embodiment, rod acceptor 350 is a horizontal rod acceptor configured to connect plates 310 to at least one horizontal rod. In another embodiment, rod acceptor 350 is a polyaxial rod acceptor configured to connect plates 310 to at least one of a vertical rod, a horizontal rod, and a multiaxial rod. In one embodiment, rod acceptor 350 is a horizontal rod acceptor configured to connect plates 310 to at least one of a pedicle screw, a pedicle screw set screw, and a spinal fixative device. The pedicle screw may comprise a multiaxial pedicle screwhead configured to connect to at least one of a vertical rod, a horizontal rod, and a multiaxial rod. In another embodiment, rod acceptor 350 is configured to operatively connect plates 310 to any of a variety of preexisting fixation constructs.

Figure 4:
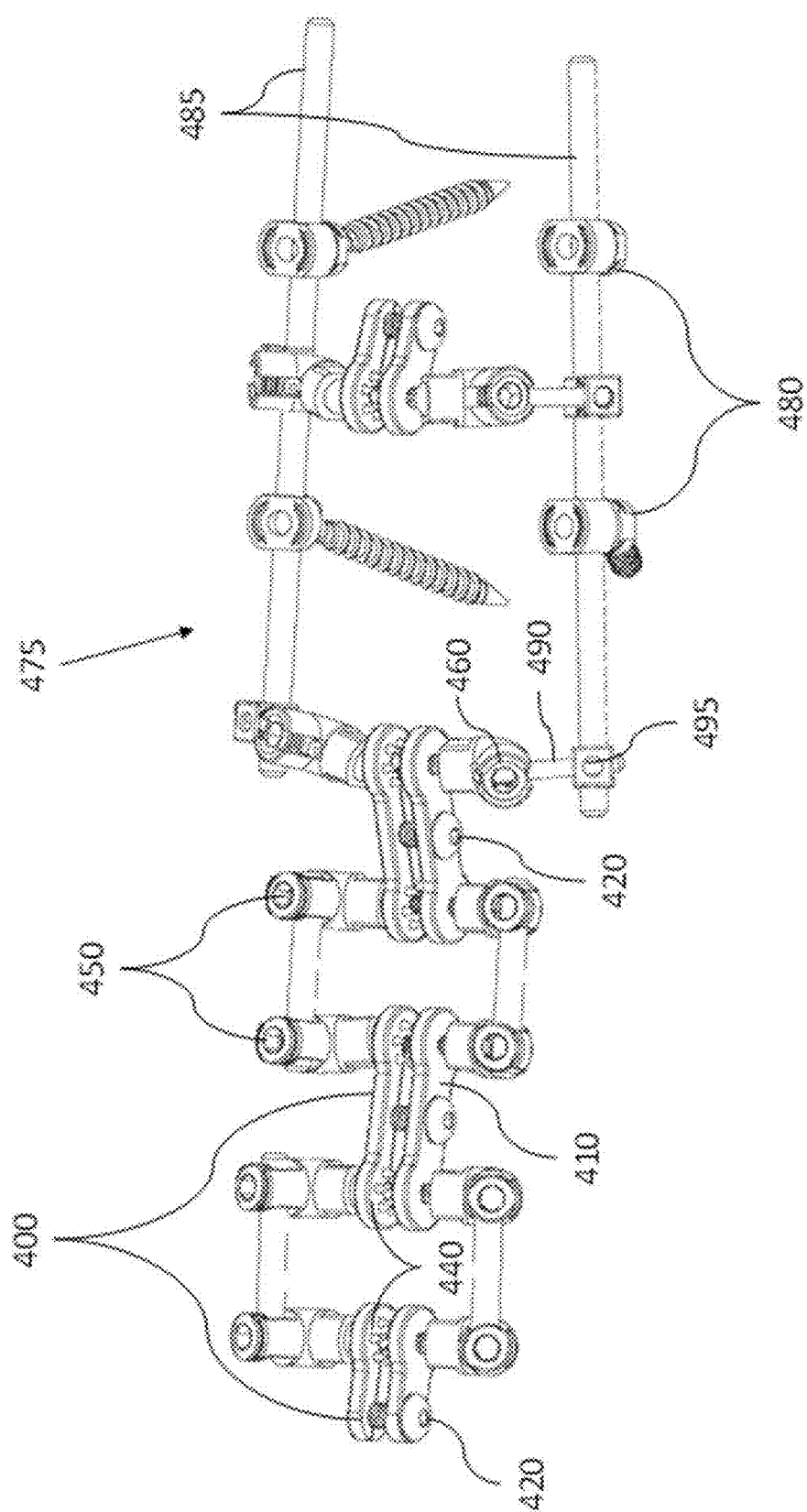
FIG. 4 illustrates an example arrangement of a system for stabilization of a spinous process.

FIG. 4 illustrates an example arrangement of a system for stabilization of a spinous process. The system comprises a spinous process clamp apparatus 400 comprising a pair of plates 410, a plate locking mechanism 420 configured to apply a compressive force upon each of the pair of plates 410. At least one of pair of plates 410 may comprise bone spikes 440. The system may also include a rod acceptor 450 and 460. In one embodiment, the system further comprises a preexisting pedicle screw construct 475, comprising at least one of a pedicle screw 480, a vertical rod 485, a horizontal rod 490, and a multiaxial rod (not shown). Rod acceptor 450 may be utilized to connect clamp apparatus 400 to at least one of vertical rod 485, horizontal rod 490, and the multiaxial rod (not shown). Clamp apparatus 400 may be configured to contact at least one spinous process.

In one embodiment, the system may further comprise a second spinous process clamp apparatus 400 configured to contact one or more spinous processes. Rod acceptor 450 may be operatively connected to second spinous process clamp apparatus.

In one embodiment, at least one spinous process clamp apparatus 400 is connected to at least one spinous process. Rod acceptor 450 may be a horizontal rod acceptor configured to engage a horizontal rod 490. Horizontal rod 490 may be connected to at least one of an acceptor component 495, a pedicle screw 480, and a pedicle screw set screw (not shown). In this manner, it is possible to attach one or more spinous process clamp apparatuses 400 to a conventional pedicle screw construct, which may be a preexisting construct.

Previous systems required removal of any preexisting pedicle screw construct when utilizing spinous process clamps. However, the system utilizing clamp apparatus 400 and rod acceptor 450 allows for spinous process clamps to be tied directly to any preexisting pedicle screw construct.

Additionally, previous systems taught only dual spinous process clamps configured to attach directly to one another in a series, whereas the clamp apparatus 400 and rod acceptor 450 allows attachment to vertical rods, horizontal rods, pedicle screws, and pedicle screw set screws between spinous processes and clamp apparatuses as necessary.

Pedicle Replacement System

Figure 5:
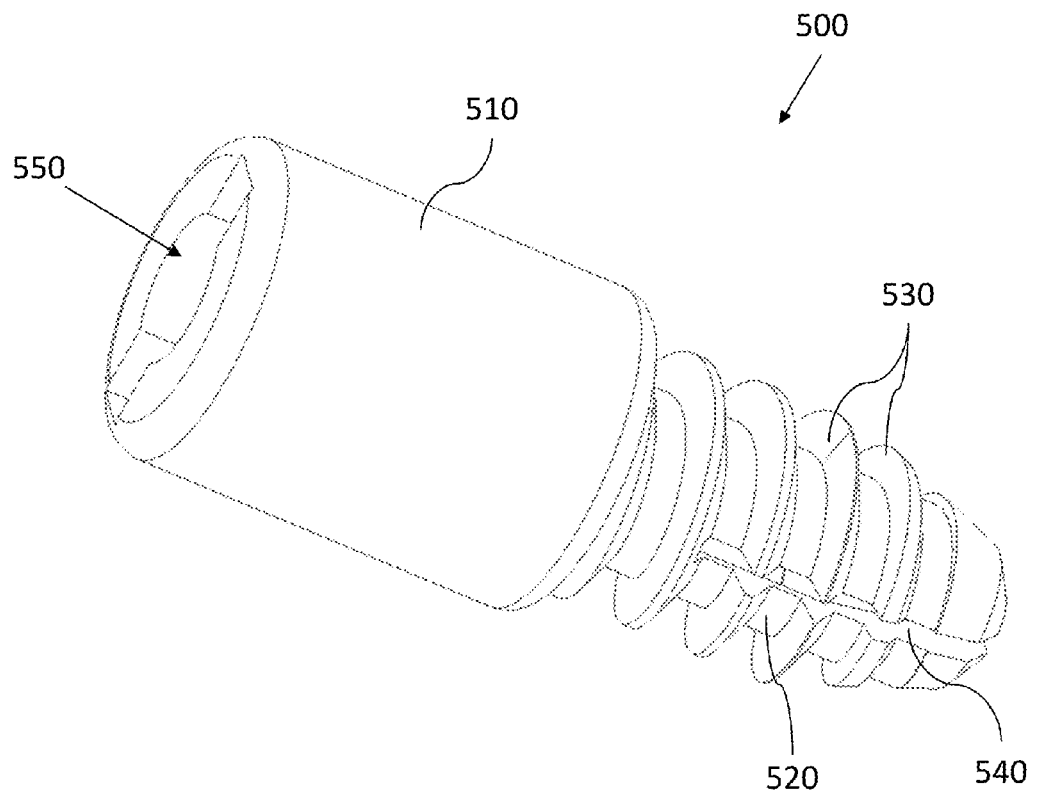
FIG. 5 illustrates an example arrangement of a pedicle prosthesis apparatus.

FIG. 5 illustrates an example arrangement of a pedicle prosthesis apparatus 500. Prosthesis apparatus 500 comprises a pedicle portion 510 configured to extend from a vertebral body and a shaft portion 520 configured to extend into the vertebral body.

Prosthesis apparatus 500 may comprise any of a variety of materials, including a metal, a polymer, or a composite.

In one embodiment, pedicle portion 510 is smooth about its exterior to avoid potential irritation by prosthesis apparatus 500 on surrounding nerves and tissue. In one embodiment, pedicle portion 510 is at least one of substantially cylindrical and substantially ellipsoidal in shape. Pedicle portion 510 may comprise any of a variety of materials, including a metal, a polymer, and a composite.

In one embodiment, prosthesis apparatus 500 comprises threads 530 configured to engage the interior of a vertebral body. In one embodiment, threads 530 are configured to engage a pre-tapped threaded hole in the vertebral body. In another embodiment, threads 530 are configured to cut into and engage a substantially smooth hole in the vertebral body. In one embodiment, threads 530 are configured to hold prosthesis apparatus 500 in place within and against the vertebral body. Threads 530 may comprise any of a variety of materials, including a metal, a polymer, and a composite.

In one embodiment, prosthesis apparatus 500 comprises barbs configured to engage the interior of a vertebral body. In one embodiment, the barbs are configured to engage a hole in the vertebral body comprising an element for mating with the barbs. In another embodiment, the barbs are configured to cut into and engage a substantially smooth hole in the vertebral body. In one embodiment, the barbs are configured to hold prosthesis apparatus 500 in place within and against the vertebral body. The barbs may comprise any of a variety of materials, including a metal, a polymer, and a composite.

In one embodiment, shaft portion 520 comprises a distal end having at least one aperture 540. At least one aperture 540 may comprise a series of longitudinal slits extending at least substantially through shaft portion 520 and configured to permit the expansion of shaft portion 520 upon manipulation of at least one aperture 540. In one embodiment, at least one aperture 540 allows shaft portion 520 to expand and engage the interior of the vertebral body, which expansion may cause a force at least substantially transverse to shaft portion 520. This expanding action of shaft portion 520 may help prevent unscrewing and/or loosening of prosthesis apparatus 500.

In one embodiment, prosthesis apparatus 500 further comprises a substantially hollow interior portion 550 configured to accept a pedicle screw (not shown). In one embodiment, the pedicle screw may be inserted at least partially or entirely through substantially hollow interior portion 550. In another embodiment, the pedicle screw may be inserted into substantially hollow interior portion 550. In one embodiment, upon insertion of a pedicle screw into substantially hollow interior portion 550, the pedicle screw causes manipulation of at least one aperture 540, thereby causing expansion of shaft portion 520. In another embodiment, substantially hollow interior portion 550 comprises threads. The threads may comprise female threads configured to substantially mate with male threads of a pedicle screw.

In one embodiment, substantially hollow interior portion 550 does not comprise threads, but is configured to engage the threads of a pedicle screw inserted therein. In one embodiment, substantially hollow interior portion 550 comprises a surface having a hardness that is low enough to permit engagement of the pedicle screw threads therein. For example, the surface of substantially hollow interior portion 550 may comprise a silicone material capable of accepting the threads of a pedicle screw. In one embodiment, substantially hollow interior portion 550 comprises a surface that is soft enough to engage pedicle screw threads therein. In another embodiment, substantially hollow interior portion 550 comprises a surface configured to plastically deform upon insertion of pedicle screw threads therein, wherein the plastic deformation engages the surface of substantially hollow interior portion 550 with the pedicle screw threads. In another embodiment, the surface of substantially hollow interior portion 550 may comprise a bone graft material capable of accepting the threads of a pedicle screw.

Figure 6:
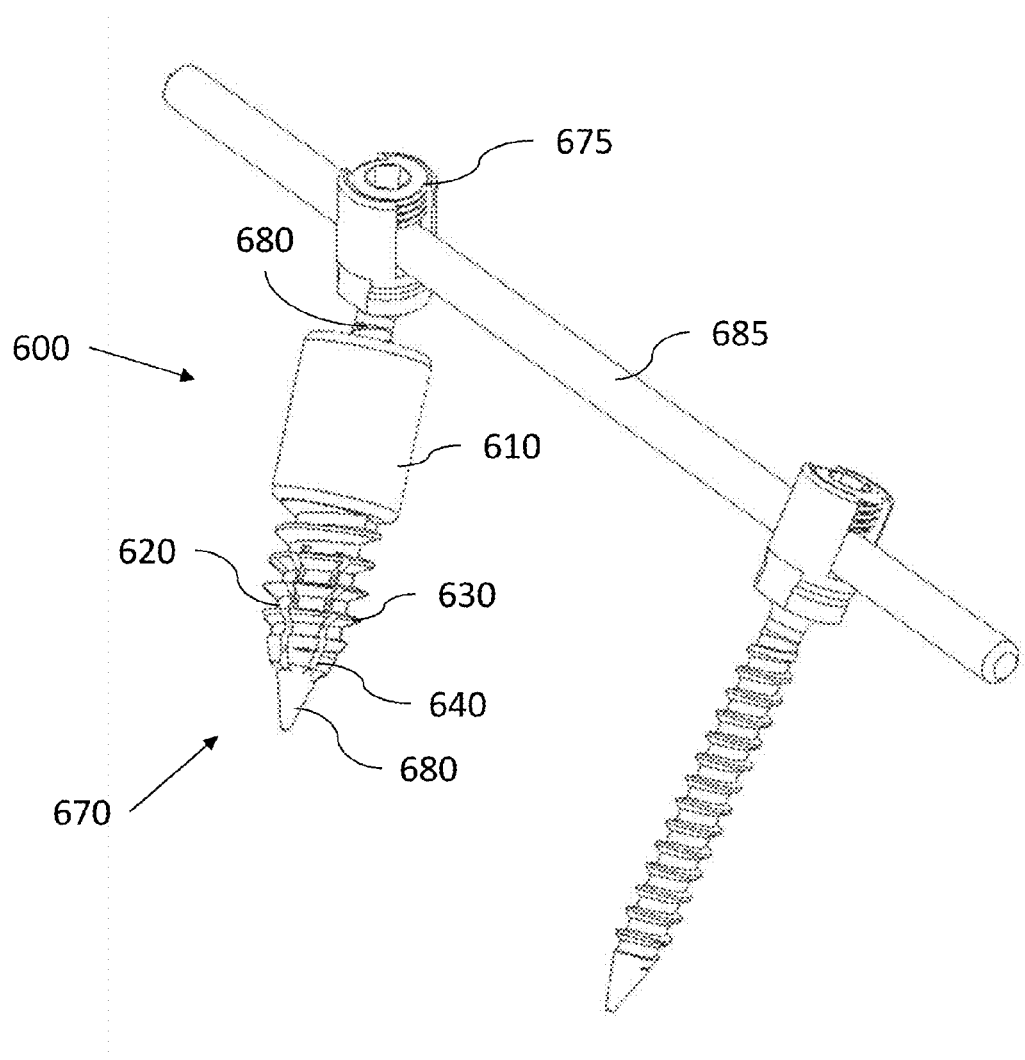
FIG. 6 illustrates an example arrangement of a system for replacement of a pedicle of a vertebral body.

FIG. 6 illustrates an example arrangement of a system for replacement of a pedicle of a vertebral body. The system comprises a pedicle prosthesis apparatus 600 comprising a pedicle portion 610, a shaft portion 620 and a substantially smooth exterior. Pedicle prosthesis 600 may additionally include threads 630 and at least one aperture 640. The system may additionally comprise at least one pedicle screw set screw 675 and at least one pedicle screw 680. The system may further comprise at least one fixation rod 685.

In one embodiment, the system further comprises at least one of a fixation rod 685, a crosslink, and a spinous process clamp. In this embodiment, the at least one pedicle screw 680 is configured to operatively connect to at least one of the fixation rod 685, the crosslink, and the spinous process clamp. In one embodiment, the at least one pedicle screw 680 is configured to operatively connected to at least one of a vertical fixation rod, a horizontal fixation rod, and a multiaxial fixation rod. In another embodiment, the at least one pedicle screw 680 is configured to interface with a spinal fixation system. In another embodiment, the at least one pedicle screw 680 is configured to operatively connect to at least one of the fixation rod 685, the crosslink, and the spinous process clamp through a pedicle screw set screw 675.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. To the extent that the term "horizontal" or "vertical" is used in the specification or the claims, it is intended to mean that the identified components are substantially horizontal or substantially vertical, respectively, when installed in a human that is standing in an upright position. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A minimally invasive crosslink apparatus, the apparatus comprising:
 a substantially straight and substantially smooth thread-free elongated shaft portion;
 a self-drilling tip portion, the self-drilling tip portion comprising a fluted end, such that rotation of the self-drilling tip portion with the fluted end creates a passage for the elongated shaft portion through a hard tissue, wherein all of the elongated shaft portion is capable of advancing axially through the hard tissue without engagement of the hard tissue by the elongated shaft portion, and wherein the elongated shaft portion is not engaged to the hard tissue by any hardware connected to the elongated shaft portion; and
 a posterolateral delivery device, the posterolateral delivery device comprising a driver engagement portion configured to connect the posterolateral delivery device to a driver device, and wherein the driver device is configured to cause at least one of a torque and a lateral force upon the self-drilling tip portion about a longitudinal axis of the elongated shaft portion;
 wherein the elongated shaft portion is configured to connect to at least one of a vertical fixation rod and a pedicle screw head.

2. The apparatus of claim 1, wherein the self-drilling tip portion is configured to create a passage for the elongated shaft portion through a soft tissue.

3. The apparatus of claim 1, wherein the self-drilling tip portion is configured to create a passage for the elongated shaft portion through at least one of bone, muscle, fascia, and fat.

4. The apparatus of claim 1, wherein the posterolateral delivery device is selectively removable from the elongated shaft portion.

5. The apparatus of claim 1, wherein the elongated shaft portion is configured to connect to the vertical fixation rod through at least one acceptor component.

6. The apparatus of claim 5, wherein the at least one acceptor component comprises a fastener configured to attach the elongated shaft portion to the vertical fixation rod.

7. The apparatus of claim 1, wherein the pedicle screw head comprises a pedicle screw set screw.

8. A system for spinal fusion, the system comprising:
 a minimally invasive crosslink apparatus comprising an elongated shaft portion and a self-drilling tip portion, wherein the self-drilling tip portion is configured to create a passage for the elongated shaft portion through a hard tissue by drilling the passage through the hard tissue using a rotational motion, wherein the elongated shaft portion is capable of advancing axially through the hard tissue without engagement of the hard tissue by the elongated shaft, and wherein the elongated shaft portion does not require rotational motion to axially advance through the hard tissue, and wherein the elongated shaft portion is not engaged to the hard tissue by any hardware connected to the elongated shaft portion;
 at least one of a vertical fixation rod and a pedicle screw set screw; and
 wherein the elongated shaft portion is connected to at least one of the vertical fixation rod and the pedicle screw set screw.

9. The system of claim 8, wherein the self-drilling tip portion is configured to create a passage for the elongated shaft portion through a soft tissue.

10. The system of claim 8, wherein the self-drilling tip portion is configured to create a passage for the elongated shaft portion through at least one of bone, muscle, fascia, and fat.

11. The system of claim 8, wherein the elongated shaft portion is configured to connect to at least one of the vertical fixation rod and the pedicle screw set screw through at least one acceptor component.

12. The system of claim 8, further comprising at least one acceptor component comprising a fastener configured to attach the elongated shaft portion to the vertical fixation rod.

13. The system of claim 8, further comprising at least one acceptor component comprising a set screw configured to attach the elongated shaft portion to the vertical fixation rod.

14. A method for installing a minimally invasive crosslink apparatus for spinal fusion, the method comprising:
   providing a pedicle screw construct comprising a pedicle screw, a pedicle screw head, a pedicle screw set screw, and at least one vertical fixation rod;
   providing a minimally invasive crosslink apparatus comprising an elongated shaft and a self-drilling tip portion, wherein the self-drilling tip portion is configured to create a passage for the elongated shaft through a hard tissue by drilling the passage through the hard tissue using a rotational motion, such that all of the elongated shaft is free to advance axially through the hard tissue without engagement of the hard tissue by the elongated shaft and without rotational motion of the elongated shaft;
   connecting at least one acceptor component to one or more of the at least one pedicle screw set screw and the at least one vertical fixation rod;
   connecting the minimally invasive crosslink apparatus to a driver device;
   activating the driver device to cause at least one of a torque and a lateral force upon the self-drilling tip portion;
   advancing the minimally invasive crosslink apparatus along its longitudinal axis: (1) medially from a first side of the spinal column in a plane substantially parallel to a frontal plane, (2) across the midsagittal plane, and (3) laterally to a second side of the spinal column in a plane substantially parallel to the frontal plane, and
   connecting the elongated shaft to the at least one acceptor component.

15. The method of claim 14, wherein the minimally invasive crosslink apparatus further comprises a posterolateral delivery device, and wherein the posterolateral delivery device is connected to the driver device.

16. The method of claim 15, further comprising removing the posterolateral delivery device from the minimally invasive crosslink apparatus following the advancing the minimally invasive crosslink apparatus along its longitudinal axis.

17. The method of claim 14, wherein the advancing the minimally invasive crosslink apparatus along its longitudinal axis further comprises causing the self-drilling tip portion to create a passage for the elongated shaft portion through at least one of a hard tissue and a soft tissue.

18. The method of claim 14, wherein the advancing the minimally invasive crosslink apparatus along its longitudinal axis further comprises causing the self-drilling tip portion to pass through the at least one acceptor component.

* * * * *